United States Patent [19]
Renz et al.

[11] Patent Number: 6,157,193
[45] Date of Patent: Dec. 5, 2000

[54] MR IMAGING SYSTEM WITH ELECTRICALLY INSULATED COIL ELEMENT

[75] Inventors: Wolfgang Renz; Markus Vester, both of Erlangen, Germany

[73] Assignee: Siemens Aktiengesellschaft, Munich, Germany

[21] Appl. No.: 09/195,488

[22] Filed: Nov. 18, 1998

[30] Foreign Application Priority Data

Nov. 18, 1997 [DE] Germany .......................... 197 51 017

[51] Int. Cl.⁷ .................................................. G01V 3/00
[52] U.S. Cl. ................................... 324/318; 600/422
[58] Field of Search .................................. 324/318, 322, 324/300, 314, 307, 309; 600/422, 423, 424

[56] References Cited

U.S. PATENT DOCUMENTS

| | | | |
|---|---|---|---|
| 5,396,905 | 3/1995 | Newman et al. | 324/318 |
| 5,735,278 | 4/1998 | Hoult et al. | 324/322 |

FOREIGN PATENT DOCUMENTS

| | | |
|---|---|---|
| 0437049A2 | 7/1991 | European Pat. Off. . |
| 3500456C2 | 9/1994 | Germany . |
| 43240121A1 | 1/1995 | Germany . |
| 19618988A1 | 11/1997 | Germany . |

OTHER PUBLICATIONS

"Intraoperative Diagnostic and Interventional Magnetic Resonance Imaging in Neurosurgery", Volker Tronnier et al., Neurosurgery, vol. 40, No. 5, May 1997.

*Primary Examiner*—Louis Arana
*Attorney, Agent, or Firm*—Herbert L. Lerner; Laurence A. Greenberg; Werner H. Stemer

[57] ABSTRACT

An MR imaging system with an electrically insulated coil element includes at least one first coil element which is electrically connected to an electronic unit and at least one electrically completely insulated second coil element which is magnetically coupled to the first coil element. Operative interventions in a region to be examined are possible through a free access area. The sterility that is necessary during operations is ensured by a device for shielding from germs.

20 Claims, 3 Drawing Sheets

MR IMAGING SYSTEM WITH ELECTRICALLY INSULATED COIL ELEMENT

BACKGROUND OF THE INVENTION

Field of the Invention

The invention relates to an imaging system based on nuclear magnetic resonance, including an RF coil device for the excitation of nuclei in a patient region to be examined and for the detection of signals emitted by the excited nuclei, the RF coil device having at least one first coil element, and at least one electrically completely insulated second coil element magnetically coupled to the first coil element for amplifying the signals emitted from the region to be examined. A corresponding imaging system is disclosed, for example, by German Patent DE 35 00 456 C2.

During operative interventions in the human organism, the requirement that an imaging system be used to monitor the operative procedures as well as the region of the body undergoing treatment is being imposed more and more frequently. In principle, all of the imaging methods which are customary at the present time in medical technology are suitable for that purpose, such as computer tomography (CT), ultrasound or magnetic resonance (MR) methods. On one hand, CT methods make use of ionizing X-rays, which are known to put a strain both on the patient's body and on the surgeon's body. On the other hand, during ultrasound monitoring of tumor operations, the image quality can be impaired by artifacts as a consequence of blood accumulations. As a result, the important statement of diagnosis regarding whether it has been possible to completely eliminate a tumor or whether residues still remain, becomes impossible under certain circumstances or is at the very least rendered more difficult. By contrast, MR methods exhibit a better image quality precisely during the imaging of soft tissue, so that they are particularly well suited to the application described.

MR imaging systems, which generate sectional images of an object to be examined, in particular of a human body or body part, using nuclear magnetic resonances, are known per se. In that case, the body to be examined is introduced into a strong, homogeneous, static magnetic field, a so-called background field, which effects alignment of nuclear spins of atomic nuclei, in particular of hydrogen atom nuclei (protons) bound to water, in the body. Those nuclei are then excited to effect precessional motion through the use of radio frequency excitation pulses. After the end of a corresponding radio frequency excitation pulse, the atomic nuclei precess with a frequency depending on the strength of the background field and then settle back into a preferred direction, predetermined by the background field, due to their spins at a predetermined relaxation time. Computational and/or measurement analysis of the integral, radio frequency signals from the nuclei can be used to generate an image, with regard to a layer of the body, from the spatial spin density or from the distribution of the relaxation times. Linear field gradients are used to assign the nuclear resonance signal, which can be detected due to the precessional motion, to the location where it originated. For that purpose, corresponding gradient fields are superposed on the background field and controlled in such a way that the nuclei are excited only in a layer to be imaged. An RF coil device is necessary both for radio frequency (RF) excitation of the nuclear spins and for detection of the response signals from the nuclei. Imaging systems based on those physical effects are also known under the designations nuclear spin tomography, nuclear magnetic resonance (NMR) tomography or magnetic resonance imaging (MRI).

A paper entitled "Intraoperative Diagnostic and Interventional Magnetic Resonance Imaging in Neurosurgery" by V. M. Tronnier et al., in *Neurosurgery*, Vol. 40, No. 5, May 1997, pages 891 to 902 describes an interventional MR imaging system constructed for use in neurosurgery for the purpose of monitoring operative interventions. In that case, use is made of an RF coil formed of two separate partial areas connected through the use of contact connectors. The first separate coil part remains unsterile, whereas the second coil part and the two contact connectors must be sterile since they are in direct proximity to the treatment region and, consequently, must satisfy the specific requirements of sterility during operations. In that context, sterility is to be understood to mean the maximum number of germs in the surroundings of the treated body parts, in particular of open operation wounds, which is usually permissible in the case of medical interventions. In order to avoid consequential infections of the wounds, absolute freedom from germs is striven for in that case. The structure described consequently requires special measures for sterilization which can turn out to be complicated precisely for the contact connectors. The same applies to electrical supply leads of RF coils if they are likewise routed through the sterile area, as is customary in other devices.

German Patent DE 35 00 456 C2 discloses an RF coil device for an MR imaging system in which, in addition to a first RF coil connected to the electronic unit, a second RF coil is also used. The second RF coil is electrically completely insulated from the surroundings. The two coils are magnetically coupled, with the result that signals received by the second RF coil from a region to be examined are coupled over into the first RF coil, from where they reach the connected electronic evaluation unit. In that case, the second RF coil is closer to the region to be examined than the first RF coil. Signal amplification is the aim of the specific configuration disclosed, having two magnetically coupled RF coils. Since the magnetic flux is concentrated through the second coil in a targeted manner in the region to be examined, the desired increase in the signal levels is thus achieved. However, there are no statements in that publication regarding the specific requirements which have to be satisfied by the RF coil device if it is to be used in connection with operative measures on the region to be examined. Rather, the RF coil devices disclosed in the exemplary embodiments of that device would make an operative intervention taking place in parallel with the MR imaging appear to be impossible.

SUMMARY OF THE INVENTION

It is accordingly an object of the invention to provide an MR imaging system with an electrically insulated coil element, which overcomes the hereinafore-mentioned disadvantages of the heretofore-known devices of this general type, in which evaluated image signals have a high signal-to-noise (S/N) ratio, that is to say a high signal gain, and which is at the same time suitable for an operative intervention in a region to be examined that takes place in parallel with the MR imaging.

With the foregoing and other objects in view there is provided, in accordance with the invention, an imaging system based on nuclear magnetic resonance, comprising an RF coil device for excitation of nuclei in a patient region to be examined and for detection of signals emitted by excited nuclei, the RF coil device including at least one first coil element; at least one electrically completely insulated second coil element magnetically coupled to the first coil element for amplifying the signals emitted from the region to be examined; at least one free access area for mechanical intervention into the region to be examined, in particular for an operation or for a biopsy; and a device for shielding the region to be examined from germs.

In this case, the invention is based on the insight that the RF coil device known from the prior art and having two magnetically coupled RF coils can not only be used advantageously to afford an increase in the signal levels but also, with additional account being taken of the defining features mentioned in the previous paragraph, with particular advantage for an interventional MR imaging system. In contrast to the described prior art (RF coil divided in two with sterile and unsterile partial areas), the complicated measures for sterilization of contact connectors or else of supply leads are obviated according to the invention. Preferably, therefore, on one hand the boundary of the sterile area should be placed precisely between the two coil elements, with the result that only the second coil elements that are free from supply leads are situated within the sterile area. The first coil elements, on the other hand, are situated together with supply leads and, if appropriate, also contact connectors outside the sterile area. Due to the magnetic RF coupling of the two coil elements, signal transmission beyond the sterility boundary is ensured even without direct electrical connections, which must be regarded as potential germ bridges in this context. Furthermore, the position of the second coil elements is restricted only by sufficient magnetic coupling with respect to the first coil elements and, consequently, can be freely determined within wide limits. Positions which lead to flux concentration in the region to be examined and, as a consequence thereof, to an improved S/N ratio as compared with interventional MR imaging systems according to the prior art are particularly advantageous in this context. Due to the largely free positionability, the second coil elements can, moreover, be positioned in a simple manner and with no losses of effect in such a way that free access areas are produced for interventions in the region to be examined, such as for operations or for biopsies, for example.

In accordance with another feature of the invention, there is provided a sterile separating layer situated between the first coil element and the region to be examined. Preferably, it is also possible for more than one sterile separating layer to be present in particular in the case of a plurality of first coil elements which can, moreover, be situated on different sides of the region to be examined. In order to effectively shield the region to be examined from germs from the unsterile first coil elements, a plurality of sterile separating layers may be necessary in this case. The separating layers may be constructed as sterile covers made of fabric or, in particular, plastic. In this case, all materials which can withstand the conditions of sterilization processes are preferred. Advantageously, the separating layers are additionally constructed in such a way that they are also magnetically RF-permeable, with the result that the first coil elements can couple magnetically into the region to be examined for the purpose of transmitting and receiving RF signals.

In a further advantageous embodiment, the second coil elements are disposed within the sterile area, which surrounds the region to be examined and is delimited from the first coil elements by the separating layers. The second coil elements should preferably have a sterile construction. For this purpose, they are either themselves subjected to a sterilization process or they are surrounded completely, that is to say in a manner hermetically sealed against germs, by sterile, magnetically RF-permeable enclosures which are preferably composed of the same materials as the separating layers. Since the second coil elements have neither electrical nor mechanical connections to the outside, the hermetically sealed encapsulation can be implemented without difficulty.

In accordance with a further feature of the invention, the second coil elements are constructed in such a way that the volume which they respectively surround (that is the inner coil space) can serve as a preferred access area for operative interventions in the region to be examined. For this purpose, the inner coil space should, inter alia, preferably be large enough to be able to accommodate instruments that may be required for the operative intervention, and it should not be filled with material either. In a particularly advantageous manner, an area of the inner coil space which is near the center can be used as the access area. The instruments that may be required for the operative intervention then have a minimal influence on the magnetic coupling fields between the first and second coil elements, and the coupling fields run principally in marginal zones of the inner coil space. The area near the center in this case is to be understood to mean, for example, a likewise cylindrical area which is disposed about the coil axis and has a cross-sectional area that makes up at most 80% of the cross-sectional area of the coil, in the case of a cylindrical coil geometry. The same conditions also apply to other coil geometries.

In another preferred development of the imaging system, a plurality of electrically insulated, second coil elements are provided, which are preferably placed in such a way that their respective imaging area encompasses different partial areas of the region to be examined. As a result, signals having an improved S/N ratio can be received simultaneously from different partial areas of the region to be examined.

In accordance with an added feature of the invention, a plurality of preferably round second coil elements having, especially, different sizes can be disposed quasi-concentrically with respect to one another, resulting in an imaging area extending more deeply into the region to be examined. The second coil elements are preferably constructed as surface coils, preferably with a round cross-sectional area and in different sizes. Specifically, when there are a large number of human body parts to be examined, for example on the head, round coils can be placed, with no additional fastening measures, simply by slipping them on the region to be examined. However, it is also possible to use other coil geometries of respectively variable size depending on anatomical conditions. However, imaging systems having only a single second coil element are likewise conceivable.

In accordance with an additional feature of the invention, the second coil elements also include a capacitance device and a current limiting device. Both are preferably electrically conductively connected to the coils. In this case, the capacitance device is constructed in such a way that the resonant frequencies, which are defined by way of the capacitance and inductance values, are tuned to the respective resonances of the precessing nuclei in the region to be examined.

In accordance with yet another feature of the invention, the current limiting device may include at least one diode or alternatively, two reverse-connected parallel diodes, which serve to protect the patient. They prevent the formation of dangerous eddy currents in the patient's body regions near the coil by limiting the coil currents causing the eddy currents to a maximum value which is noncritical in this respect. In addition to increased patient protection, the current limiting device also serves to avoid field concentrations by the second coil elements during the RF transmission operation. The transmission magnetic field, which is as homogeneous as possible, consequently experiences no undesirable distortions and the excitation of the nuclei in the region to be examined then takes place largely uniformly.

In accordance with yet a further feature of the invention, the current limiting device is constituted as at least one additionally built-in fuse, which ensures that the coil current is limited in the event of failure of the diodes.

In accordance with yet an added feature of the invention, there is provided in each case at least one separate coil for transmission and for reception as first coil elements. One advantage of this division resides in the improved possibilities for an optimum structure of the individual coils with regard to their respective task. In order to correspondingly excite the nuclei in the region to be examined, the transmission coil should generate strong magnetic fields which are as homogeneous as possible in the region to be examined. In this context, as homogeneous as possible measures with a variation of less than 20%, in particular less than 15% are desired. On the other hand, the output-coupling coil used for the purpose of reception should be as sensitive as possible to the very small magnetic field strengths emitted by the nuclei as a reaction. In this case, suitable transmission coils may not only be coil formers produced from an electrical conductor but also radio frequency resonators. Output-coupling coils may likewise be constructed as coil formers produced from an electrical conductor, and in particular having only one winding. For specific applications, however, it is also advantageously possible to use embodiments with only one coil, which can be used both for the purpose of transmission and for the purpose of reception.

In accordance with yet an additional feature of the invention, turns planes of the second coil elements and a turns plane of the output-coupling coil (that is the first coil element) are directed at least approximately orthogonally with respect to one another. The spatial configuration of the second coil elements and of the output-coupling coil with respect to one another in this case is to be chosen in such a way that the magnetic coupling between the two coil elements is effected not through the use of the main fields emanating perpendicularly with respect to the turns planes in the center of the cross-sectional areas of the coils but rather through the use of laterally emanating leakage fields. A configuration of the second coil elements precisely above the center of the output-coupling coil is, consequently, in this sense just as unsuitable as an excessively great deviation from the 90° angular difference given second coil elements which are simultaneously positioned above the cross-sectional area of the output-coupling coil. The advantageous type of coupling through the use of the leakage fields means that within the scope of the limits described, an otherwise largely free positionability of the second coil elements is achieved. In the case, for example, of a horizontal configuration of a round output-coupling coil underneath the region to be examined, the second coil elements can be positioned in a vertical configuration at any desired location or around the lateral edge of the region to be examined, as long as the condition of sufficient leakage flux coupling is satisfied. Preferably, in this case the round output-coupling coil should be situated in a central position underneath the region to be examined. A smaller cross-sectional area of the output-coupling coil than the horizontal cross-sectional area of the region to be examined is likewise advantageous in this case. The system-dictated imaging quality is then identical in this case at all lateral positions for the second coil elements since the coupling through the use of the coil leakage fields always remains the same as well.

In accordance with again another feature of the invention, the turns plane of the output-coupling coil is directed at least approximately orthogonally with respect to the static background field. In this embodiment variant, the main field of the output-coupling coil, the main field emanating perpendicularly with respect to the turns plane in the center of the cross-sectional area of the coil, then runs at least approximately parallel to the background field. As a result, the output-coupling coil advantageously makes virtually no contribution of its own to the reception signal. Consequently, the reception signal is almost exclusively determined by the second coil elements, which pick up the response signals emitted by the nuclei, amplify them and communicate them to the output-coupling coil. This advantageous variant avoids undesirable interference, which reduces the image quality, between reception signal components from the second coil elements and those of the output-coupling coil.

In accordance with a concomitant feature of the invention, the imaging system is developed in such a way that a transmission magnetic field generated by the transmission coil has a profile, at the location of the output-coupling coil, running at least approximately parallel to the turns plane of the output-coupling coil. In this case, there is advantageously no, or only very little, magnetic coupling between the transmission coil and the output-coupling coil. Consequently, this advantageous development makes a considerable contribution to the fact that the strong transmission magnetic fields engender no currents in the output-coupling coil which are excessively high for patient protection.

The directions at least approximately orthogonally or approximately parallel in this case are to be understood respectively to mean all corresponding orientations lying in an angular range of ±30°, preferably of ±20°, about the exact normal direction (=90° angular difference) or about the exact parallel alignment (=0° angular difference).

Other features which are considered as characteristic for the invention are set forth in the appended claims.

Although the invention is illustrated and described herein as embodied in an MR imaging system with an electrically insulated coil element, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
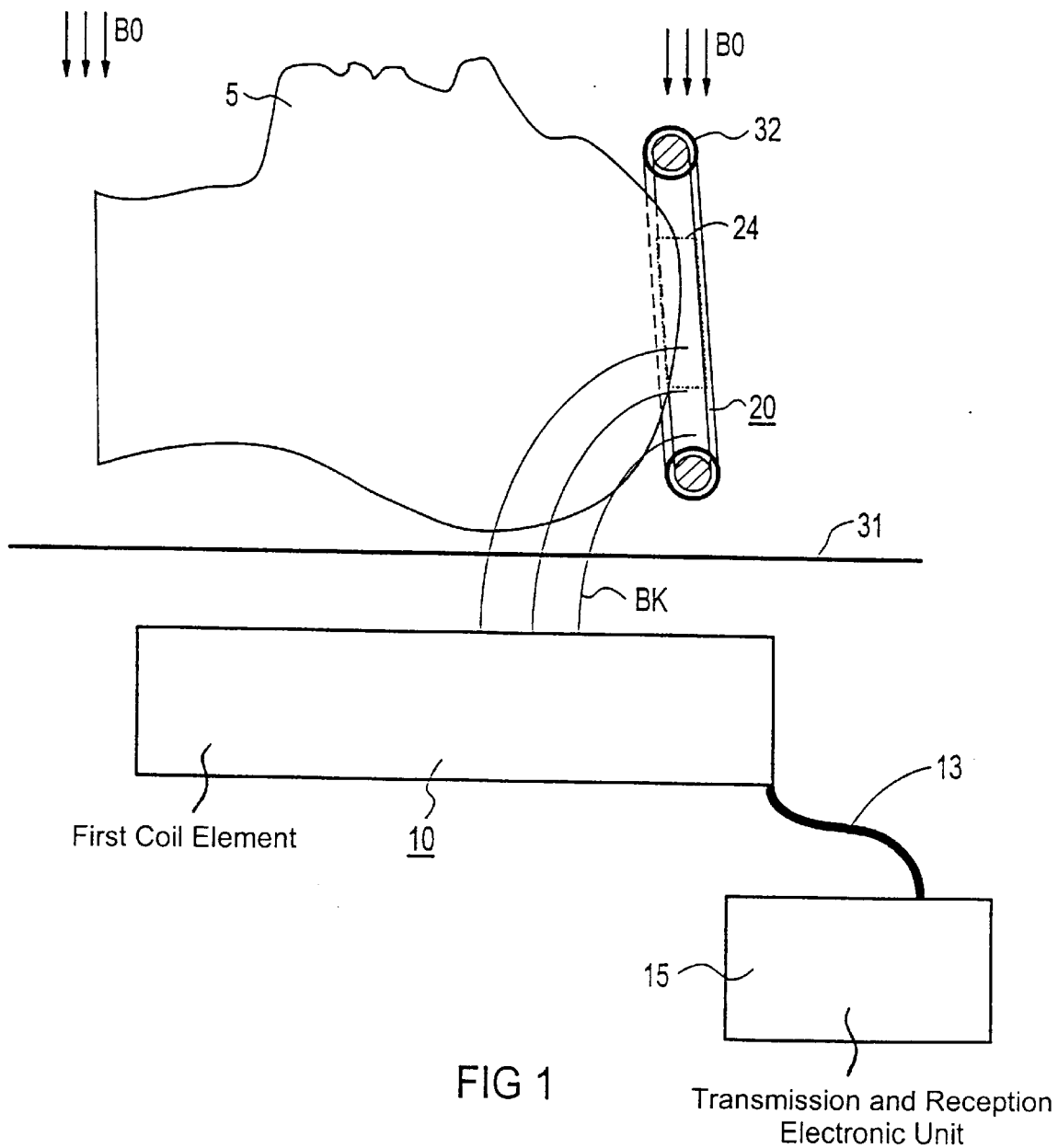
FIG. 1 is a diagrammatic, lateral cross-sectional view of an interventional MR imaging system with first and second coil elements magnetically coupled to one another.

Referring now in detail to the figures of the drawings, in which mutually corresponding parts are provided with the same reference symbols, and first, particularly, to FIG. 1 thereof, there is seen a diagrammatic, cross-sectional view of an interventional MR imaging system with a first coil element 10 and a second coil element 20, that are magnetically coupled to one another through a coupling magnetic field BK. The first coil element 10 serves not only for exciting nuclei in a patient region 5 to be examined but also for detecting response signals emitted by the excited nuclei. The first coil element 10 is connected to a transmission and reception electronic unit 15 through electrical leads 13. In contrast, the second coil element 20 has an electrically insulated structure, that is to say without any electrically conductive connection to the surroundings. The second coil element 20 receives the response signals emitted by the nuclei of the region 5 to be examined, due to their excitation by the first coil element 10. The second coil element 20 is in direct proximity to the region 5 to be examined, in this case a human head.

If required, it is also possible to slip a portion over the head. For this purpose, various geometries and sizes are provided for the second coil element 20, with the result that the latter is always matched to the respectively prevailing anatomical conditions. The imaging system is also suitable for examining other parts of the human body, for example the human knee. The imaging system with the two coil elements 10 and 20 is properly used to monitor operative interventions in the region 5 to be examined. A free access area 24 is provided for this purpose in an inner coil space of the second coil element 20. A surgeon can perform the operative intervention on the region 5 to be examined using medical instruments within this free access area 24. The intervention is monitored through the use of the second coil element 20, having a preferred imaging area that encompasses precisely the operation region.

The second coil element 20 transmits the received response signals with an improved signal-to-noise ratio through the coupling field BK to the first coil element 10 and, consequently, to the electronic unit 15 connected there, for the purpose of evaluation. The second coil element 20 effects concentration of the magnetic flux density in the region 5 to be examined as a result of the proximity to the region 5 to be examined, as a result of the coil geometry, as a result of the orientation or as a result of a combination of these features. Therefore, reception signals having a higher signal level are the result.

Prior to the excitation by the first coil element 10, preferred magnetic directions (spins) of the nuclei in the region to be examined were uniformly aligned by a static background field B0, which is generated by a non-illustrated external magnet of the Siemens MR imaging system Magnetom Open. In this case, the field strength of the background field B0 is approximately 0.2 T.

In order to ensure the sterility which is required during operations, a sterile separating layer 31, in the form of a sterile fabric cover, is provided between the region 5 to be examined and the first coil element 10. In addition, the second coil element 20 is situated in an encapsulation 32 which is impermeable to germs. The encapsulation 32 and the separating layer 31 are both magnetically RF-permeable, with the result that the requisite magnetic coupling between the first and second coil elements 10 and 20 continues to be ensured.

Figure 2:
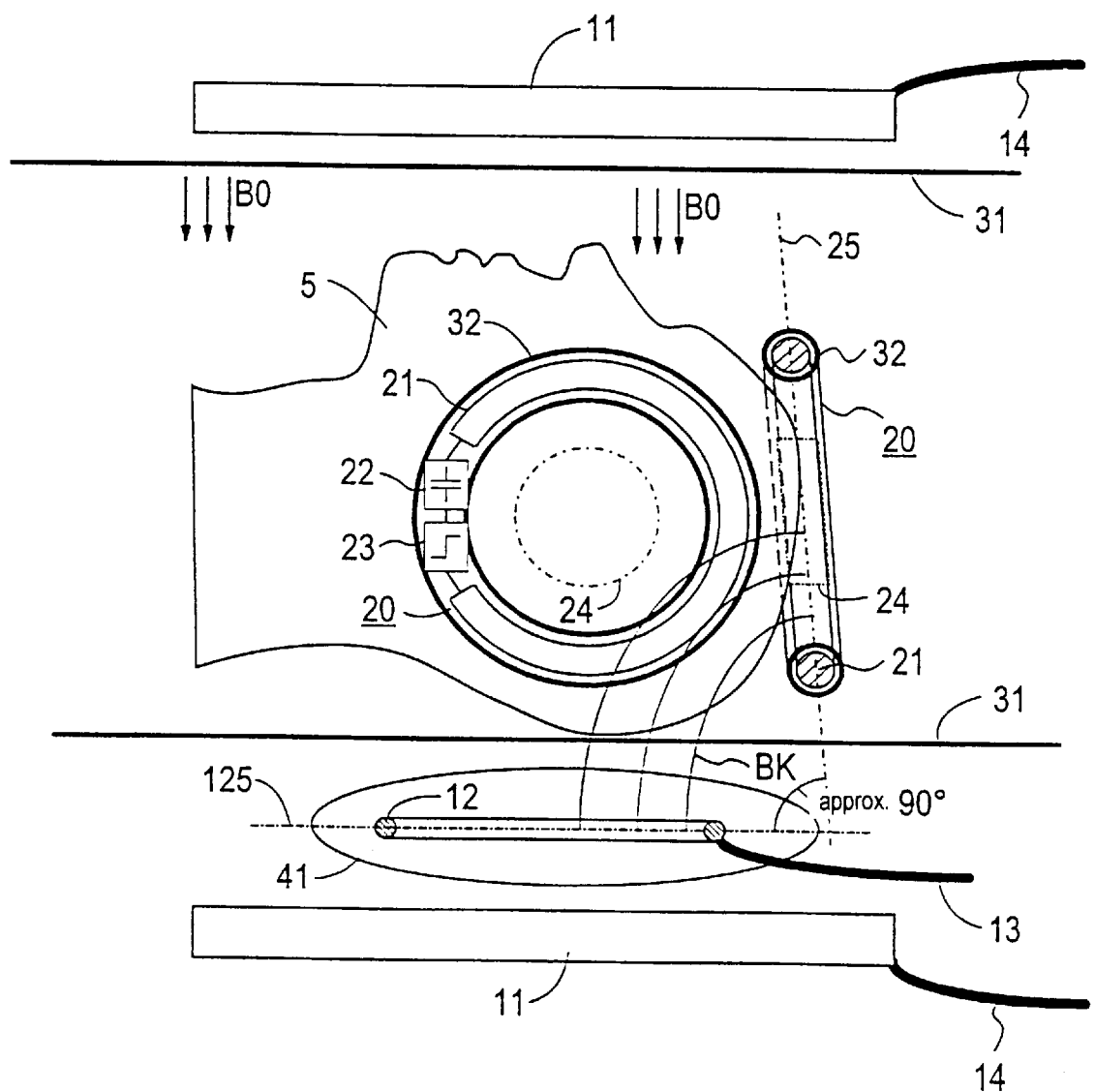
FIG. 2 is a lateral cross-sectional view of an interventional MR imaging system with a two-part transmission coil, an output-coupling coil and two surface coils magnetically coupled to the output-coupling coil.

The lateral cross-sectional view of FIG. 2 shows an MR imaging system which is further refined in comparison with FIG. 1. In this exemplary embodiment, a transmission coil 11 divided in two, in this case a transmission resonator divided in two, as well as an output-coupling coil 12, are provided as first coil elements 10. The transmission coil 11 divided in two and the output-coupling coil 12 are connected to the transmission and reception electronic unit 15 through electrical leads 13 and 14. One portion of the transmission coil 11 is situated underneath the region 5 to be examined, and the other portion is situated thereabove. The region 5 to be examined is shielded from both parts of the transmission coil 11 in a manner impermeable to germs through the use of respectively separate separating layers 31. The output-coupling coil 12 is positioned approximately 7 cm above the lower part of the transmission coil 11. The output-coupling coil 12 is situated inside a support 41, in this case a pillow, on which the region 5 to be examined, in this case the human head, is placed during treatment. The output-coupling coil 12 has a round geometry with a diameter of about 17 cm for adaptation to the shape of the head. The output-coupling coil 12 is constructed as a wire strap having one turn.

In the exemplary embodiment of FIG. 2, there are two second coil elements 20 which are each constructed as round surface coils 21 each having one turn. An electrical conductor for one turn has a diameter of approximately 1 cm. In FIG. 2, two of these surface coils 21 are positioned on the region 5 to be examined in order to monitor an operative intervention. The diameters of the surface coils 21 being used are approximately 14.4 cm and 20 cm. However, it is also possible to use surface coils 21 having different geometrical shapes and sizes. In addition, it is possible to use just one surface coil 21 or else more than the two surface coils 21 which are illustrated, for the purpose of monitoring the region 5 to be examined.

In order to achieve good coupling through the coupling field BK to the output-coupling coil 12, turns planes 25 of the surface coils 21 are directed approximately orthogonally with respect to a turns plane 125 of the output-coupling coil 12. However, all positions all around the region 5 to be examined are otherwise possible for the surface coils 21 by complying with this orientation condition and the likewise to be complied with condition of sufficient leakage field coupling. This results in very high flexibility.

The surface coils 21 are electrically conductively connected to a capacitance device 22 for the purpose of resonant tuning to the resonance of the precessing nuclei in the region 5 to be examined. A current limiting device 23, in the form of two reverse-connected parallel diodes and a fuse, are furthermore provided and are intended to prevent the patient from being put at risk from eddy currents caused by excessively high currents in the surface coils 21. Such dangerously high coil currents can occur when the strong magnetic fields of the transmission coils 11 couple into the surface coils 21. In order to ensure the required sterility, the complete second coil elements 20, including the surface coils 21 as well as the capacitance device 22 and the current limiting device 23, in each case are completely sealed by the sterile encapsulations 32 which are impermeable to germs.

Figure 3:
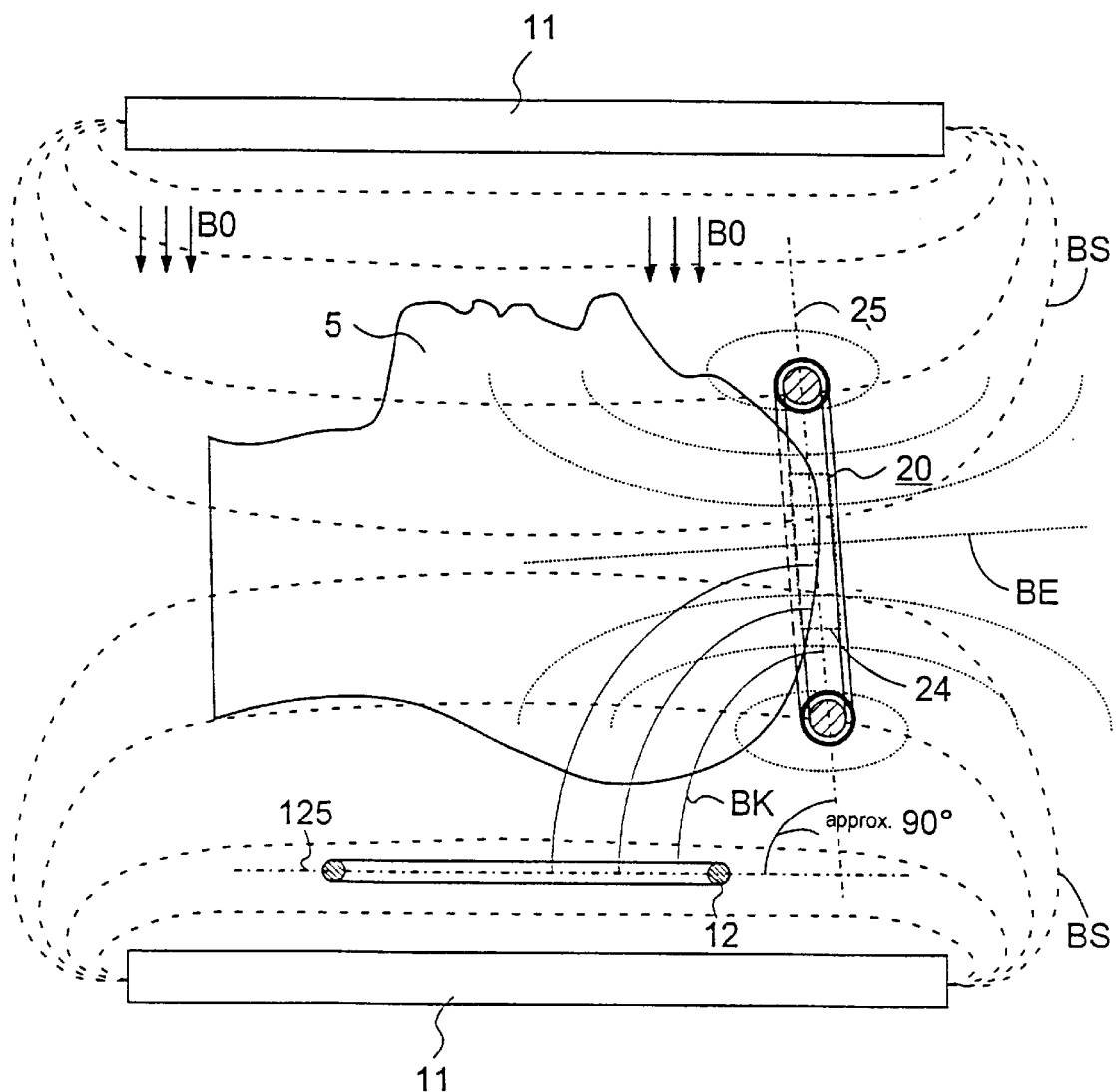
FIG. 3 is a lateral cross-sectional view showing magnetic field profiles for the interventional MR imaging system of FIG. 2.

Magnetic field profiles are illustrated in FIG. 3 in order to elucidate the functioning of the interventional MR imaging system of FIG. 2. A transmission magnetic field BS is generated by both parts of the transmission coil 11. The transmission magnetic field BS is for the most part homogeneous in the region 5 to be examined and has a profile running largely perpendicularly to the static background field B0. Under these preconditions, the nuclear spins are effectively excited in the region 5 to be examined. The transmission magnetic field BS runs largely parallel to the turns plane 125 of the output-coupling coil 12 at the location of the output-coupling coil 12. As a result, there is only very slight magnetic coupling into the output-coupling coil 12, thereby minimizing the risk of impermissibly high currents in the output-coupling coil 12. The current limiting device, which is also required for the output-coupling coil 12 and is not specifically shown in this case, is relieved by the advantageously weak coupling described herein. In contrast, the magnetic field lines of the transmission magnetic field BS permeate at least the turns plane 25 of the surface coil 21 shown in FIG. 3, with the result that the current limiting device 23 described herein is necessary in this case.

Reception fields BE detected by the surface coils 21 permeate the region 5 to be examined largely in an orthogonal orientation with respect to the background field B0, thereby accounting for the sensitivity of the surface coils 21 to the response signals of the nuclei in the region 5 to be examined. In contrast, a non-illustrated magnetic field of the output-coupling coil 12 runs largely parallel to the background field B0, with the result that the output-coupling coil 12 has no appreciable reception sensitivity of its own. The reception signals that are forwarded from the output-coupling coil 12 to the electronic unit 15 therefore originate virtually exclusively from the surface coils 21. Disturbing interference between reception signals from the surface coils 21 and those of the output-coupling coil 12 is thereby avoided. The coupling between the output-coupling coil 12 and the surface coils 21 is effected through the use of the laterally emanating leakage fields, which are designated in this case as coupling magnetic fields BK. The use of the leakage fields for coupling and the round coil geometries being used, afford the above-described great flexibility in the positioning of the surface coils 21 all around the region 5 to be examined.

We claim:

1. An imaging system based on nuclear magnetic resonance, comprising an RF coil device for excitation of nuclei in a patient region to be examined during an examination and for detection of signals emitted by excited nuclei, said RF coil device including:

a) at least one first coil element;
   b) at least one electrically completely insulated second coil element magnetically coupled to said first coil element for amplifying the signals emitted from the region to be examined;
   c) at least one free access area for mechanical intervention into the region to be examined during the examination; and
   d) a device for shielding the region to be examined from germs.

2. The imaging system according to claim 1, wherein said at least one free access area is provided for an operation or for a biopsy.

3. The imaging system according to claim 1, wherein said shielding device includes at least one sterile, magnetically RF-permeable separating layer for shielding from germs between said at least one first coil element and the region to be examined.

4. The imaging system according to claim 3, wherein said at least one separating layer is formed of plastic.

5. The imaging system according to claim 1, wherein said at least one free access area is at least one inner coil space of said at least one second coil element.

6. The imaging system according to claim 5, wherein said at least one inner coil space is disposed approximately centrally in said at least one second coil element.

7. The imaging system according to claim 1, including a support for the region to be examined, said at least one first coil element disposed within said support.

8. The imaging system according to claim 1, including an electronic unit, and electrical leads connecting said electronic unit to said at least one first coil element.

9. The imaging system according to claim 1, wherein said at least one second coil element is a surface coil.

10. The imaging system according to claim 9, wherein said surface coil has round geometry.

11. The imaging system according to claim 1, wherein said at least one second coil element includes a capacitance device and a current limiting device.

12. The imaging system according to claim 11, wherein said current limiting device includes at least one diode.

13. The imaging system according to claim 11, wherein said current limiting device includes at least one fuse.

14. The imaging system according to claim 1, wherein said at least one second coil element is sterile.

15. The imaging system according to claim 1, wherein said at least one second coil element is encapsulated in a sterile manner.

16. The imaging system according to claim 15, including a sterile encapsulation magnetically RF-permeable and completely enclosing said at least one second coil element.

17. The imaging system according to claim 1, wherein said at least one first coil element includes at least one transmission coil and at least one output-coupling coil for reception.

18. The imaging system according to claim 17, wherein said at least one second coil element has a turns plane, said output-coupling coil has a turns plane, and said turns planes are at least approximately mutually orthogonal.

19. The imaging system according to claim 17, wherein said output-coupling coil has a turns plane at least approximately orthogonal to a background magnetic field.

20. The imaging system according to claim 17, wherein said at least one transmission coil generates a transmission magnetic field, and said at least one transmission coil and said at least one output-coupling coil cause said transmission magnetic field to have a profile at a location of said at least one output-coupling coil running at least approximately parallel to said turns plane of said at least one output-coupling coil.

* * * * *